United States Patent [19]

Kabbe et al.

[11] 4,307,020
[45] Dec. 22, 1981

[54] PROCESS OF PREPARING 3-CARBOXYMETHYL-2-CARBOXY-CHROMONES

[75] Inventors: Hans-Joachim Kabbe; Paul-Ernst Frohberger, both of Leverkusen; Peter Roessler, Gladbach, all of Fed. Rep. of Germany

[73] Assignee: Bayer Aktiengesellschaft, Leverkusen, Fed. Rep. of Germany

[21] Appl. No.: 167,880

[22] Filed: Jul. 14, 1980

Related U.S. Application Data

[60] Continuation of Ser. No. 39,620, May 16, 1979, abandoned, which is a division of Ser. No. 918,129, Jun. 22, 1978, Pat. No. 4,189,498.

[30] Foreign Application Priority Data

Jul. 13, 1977 [DE] Fed. Rep. of Germany ....... 2731566

[51] Int. Cl.³ .......................................... C07D 711/22
[52] U.S. Cl. ........................... 260/345.2; 260/340.5 R; 546/89; 546/92; 549/44; 549/48
[58] Field of Search ...................... 260/345.2, 340.5 R; 546/89, 92; 549/44, 48

[56] References Cited

U.S. PATENT DOCUMENTS 3,862,143 1/1975 Klutchko et al. ................ 260/345.2
3,879,427 4/1975 Strandtmann et al. .......... 260/345.2

OTHER PUBLICATIONS

Ellis et al., JCS, Perkin I, 1974, 2570.

*Primary Examiner*—Nicky Chan
*Attorney, Agent, or Firm*—Sprung, Felfe, Horn, Lynch & Kramer

[57] ABSTRACT

2-Carboxymethyl-3-carboxy-chromones and esters of the formula

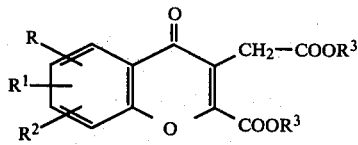

in which
R, R¹ and R² each independently is hydrogen, an optionally substituted alkyl, alkenyl, cycloalkyl, cycloalkenyl, aralkyl or aryl group, halogen, hydroxyl, cyano or an optionally substituted alkoxy aryloxy, aralkoxy, alkoxy-carbonyl or dialkylamino group, or
R and R¹, together with two carbon atoms of the benzene ring system, form a carbocyclic or heterocyclic 5-membered or 6-membered ring, and
R³ is hydrogen, optionally substituted alkyl, alkenyl, cycloalkyl, cycloalkenyl or aralkyl, are characterized by fungicidal and arthropodicidal activities. The novel compounds are produced by reacting an o-hydroxyacetophenone of the formula

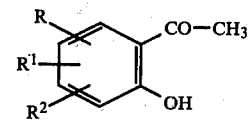

with a glyoxylic acid derivative of the formula

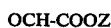

in which Z is a cation, in the presence of a basic compound, followed by acidification to form the dicarboxylic acid and, optionally, the ester.

12 Claims, No Drawings

PROCESS OF PREPARING 3-CARBOXYMETHYL-2-CARBOXY-CHROMONES

This is a continuation of application Ser. No. 039,620, filed May 16, 1979, now abandoned, which in turn is a division of application Ser. No. 918,129, filed June 22, 1978, now U.S. Pat. No. 4,189,498.

The present invention relates to certain new chromone derivatives, to an unobvious process for their preparation and to their use as plant protection agents.

It is already known that aromatic aldehydes react with o-hydroxyacetophenones in the presence of sodium hydroxide solution to give 2-phenyl-chromanones (Elderfield, "Heterocyclic Compounds", Vol. 2, page 347); it is also known that aliphatic aldehydes can also be reacted with o-hydroxyacetophenones to give the corresponding 2-alkylchromanines (see DT-OS (German Published Specification) No. 2,535,338). In both cases, the o-hydroxyacetophenone and aldehyde react in the molar ratio of 1:1. Further, it is known that chromones can be prepared from o-acylphenols and carboxylic acid derivatives, again in the ratio of 1:1 (see P. Karrer, "Lehrbuch der Organischen Chemie" ("Textbook of Organic Chemistry"), 13th edition, page 584, Georg Thieme Verlag, Stuttgart (1959)).

Zinc ethylene-bis-dithiocarbamate is known as a plant protection agent having a fungicidal action, and is recognized as a standard preparation which is used worldwide (see R. Wegler, "Chemie der Pflanzenschutz- und Schädlingsbekämpfungsmittel" ("Chemistry of Plant Protection Agents and Pesticides"), volume 4, page 139, Springer-Verlag, Berlin/Heidelberg/New York (1977). However, if low amounts are used, the action is not always satisfactory.

Active compounds which inhibit the metamorphosis of arthropods have only in recent times become of interest in plant protection. An example to be mentioned here is 2,2-dimethyl-6-methoxybenzopyran (Chem. Eng. News 54, 19–20 (1976).

The present invention now provides, as new compounds, the chromone derivatives of the general formula

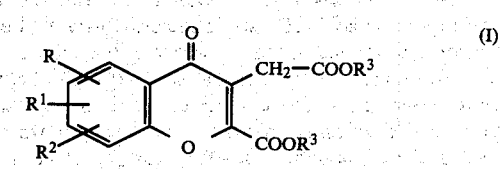

in which

R, $R^1$ and $R^2$, which need not be identical, each represent hydrogen, an optionally substituted alkyl, alkenyl, cycloalkyl, cycloalkenyl, aralkyl or aryl group, halogen, hydroxy, cyano or an optionally substituted alkoxy, aryloxy, aralkoxy, alkoxycarbonyl or dialkylamino group, or R and $R^1$, together with two carbon atoms of the benzene ring system, form a carbocyclic or heterocyclic 5-membered or 6-membered ring and $R^3$ represents hydrogen or an optionally substituted alkyl, alkenyl, cycloalkyl, cycloalkenyl or aralkyl group.

The compounds of the formula (I) possess fungicidal properties; furthermore, they inhibit the development of arthropods. They are therefore of interest as plant protection agents.

Preferably, R, $R^1$ and $R^2$, which need not be identical, each represent hydrogen, chlorine, bromine, optionally substituted, straight-chain or branched alkyl with up to 8 (preferably up to 2) carbon atoms (for example, methyl, ethyl, propyl, isopropyl, tert.-butyl or hexyl), straight-chain or branched alkenyl with one or more double bonds and up to 8 carbon atoms (preferably with up to 3 carbon atoms and one double bond) (for example, but-3-enyl and 4-methyl-pent-3-enyl), cycloalkyl or cycloalkenyl each with 3 to 8 (preferably with 4 to 6) carbon atoms (for example cyclobutyl and, especially, cyclopentyl and cyclohexyl), aryl with 6 to 10 carbon atoms (such as naphthyl and, preferably, phenyl), aralkyl of which the aliphatic part contains 1 to 8 (preferably 1 to 4) carbons and of which the aromatic part is a carbocyclic radical with 6 to 10 carbon atoms (for example phenylethyl, phenylpropyl, phenylbutyl, naphthylmethyl, naphthylethyl and, preferably, benzyl), alkoxy with up to 4 carbon atoms (such as methoxy, ethoxy, propoxy, isopropoxy, butoxy, isobutoxy and tert.-butoxy), aryloxy with 6 or 10 carbon atoms (such as phenoxy and naphthoxy), aralkoxy with 7 to 10 carbon atoms (such as benzyloxy, phenylethoxy, phenylpropoxy, phenylisopropoxy, phenylbutoxy, phenylisobutoxy and phenyl-tert.-butoxy), alkoxycarbonyl with up to 4 carbon atoms in the alkyl radical (such as methoxycarbonyl, ethoxycarbonyl, propoxycarbonyl and isopropoxycarbonyl), or dialkylamino with up to 3 carbon atoms in each alkyl radical (such as dimethylamino, diethylamino and diisopropylamino) or wherein the two alkyl radicals of the dialkylamino group are cyclized to give a ring (for example pyrrolidinyl or piperidinyl), the said alkyl, alkenyl, cycloalkyl, cycloalkenyl, aryl, aralkyl, alkoxy, aryloxy, aralkoxy, alkoxycarbonyl and dialkylamino groups optionally carrying one or more substituents selected from fluorine, chlorine, bromine, iodine, cyano, alkoxy with up to 4 carbon atoms, alkoxycarbonyl with up to 4 carbon atoms and, where substituents on ring systems are concerned, also alkyl with up to 4 carbon atoms and alkoxycarbonylalkyl with up to 4 carbon atoms, the substituted groups optionally carrying, as a further substituent, dialkylamino with a total of up to 6 (preferably up to 2) carbon atoms, carboxyl or phenyl, or R and $R^1$, with the two carbon atoms of the benzene ring on which they are located, form a cyclopentene, cyclohexene, benzene, furane, dihydrofurane, thiophene, dihydrothiophene, pyrane, dihydropyrane, pyridine or dioxolene ring.

The invention also provides a process for the preparation of a compound (I), in which an o-hydroxyacetophenone of the general formula

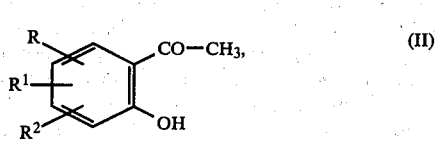

in which R, $R^1$ and $R^2$ have the above-mentioned meanings, is reacted with a glyoxylic acid derivative of the general formula

in which Z represents a cation, in the presence of a basic compound and, if desired, the dicarboxylic acid obtained after acidification (a compound of the formula (I), wherein $R^3$ represents hydrogen) is converted in a manner which is in itself known into a corresponding ester (a compound of the formula (I), wherein $R^3$ represents an optionally substituted alkyl, alkenyl, cycloalkyl, cycloalkenyl or aralkyl group).

It must be described as distinctly surprising that the o-hydroxyacetophenones of the formula (II) react with the glyoxylic acid derivatives of the formula (III) in a simple and controllable reaction to give the chromone derivatives of the formula (I) and that no chromanone compounds are formed. The discovery of the new reaction represents an enrichment of the art. It is of industrial interest that the new compounds can be used as plant protection agents.

If o-hydroxyacetophenone is reacted with the sodium salt of glyoxylic acid in the presence of pyrrolidine and the resulting dicarboxylic acid is then esterified with methanol, the course of the reaction can be represented by the following equations:

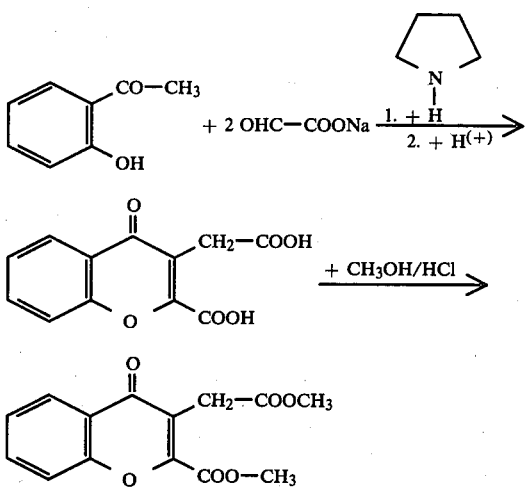

The o-hydroxy-aryl-carbonyl compounds which can be used for the process according to the invention are known (see Beilstein, Handbuch der Organischen Chemie (Handbook of Organic Chemistry), H8, page 85 et seq.). As examples there may be mentioned: o-hydroxyacetophenone, 3-chloro-2-hydroxyacetophenone, 5-chloro-2-hydroxyacetophenone, 3,5-dichloro-2-hydroxyacetophenone, 3-methyl-5-chloro-2-hydroxyacetophenone, 2,4-dihydroxyacetophenone, 2,5-dihydroxyacetophenone, 2,6-dihydroxyacetophenone, 2,3-dihydroxyacetophenone, 2,4,6-trihydroxyacetophenone, 4-pentyl-2,6-dihydroxyacetophenone, 4-heptyl-2,6-dihydroxyacetophenone, 4-(1',1'-dimethylpentyl)-2,6-dihydroxyacetophenone, 3,4-dimethoxy-6-methyl-2-hydroxyacetophenone, 3,4,6-trimethyl-2-hydroxyacetophenone, 3-methoxy-2-hydroxyacetophenone, 4-methoxy-2-hydroxyacetophenone, 5-methoxy-2-hydroxyacetophenone, 6-methoxy-2-hydroxyacetophenone, 4-benzyloxy-2-hydroxyacetophenone, 5-benzyloxy-2-hydroxyacetophenone, 4-phenoxy-2-hydroxyacetophenone, 4-cyclohexyl-2-hydroxyacetophenone, 5-phenyl-2-hydroxyacetophenone, 3-β-phenylethyl-2-hydroxyacetophenone, 5-δ-phenylbutyl-2-hydroxyacetophenone, 3,5-dibromo-2-hydroxyacetophenone, 4-ethoxy-2-hydroxyacetophenone, 5-ethoxycarbonylethoxy-2-hydroxyacetophenone, 4-methoxycarbonylmethoxy-2-hydroxyacetophenone, 4-carboxymethyl-2-hydroxyacetophenone, 5-nitro-2-hydroxyacetophenone, 3-cyano-2-hydroxyacetophenone, 4-trifluoromethyl-2-hydroxyacetophenone, 5-trifluoromethyl-2-hydroxyacetophenone, 3-trifluoromethyl-2-hydroxyacetophenone, 3-methoxycarbonyl-2-hydroxyacetophenone, 5-carboxy-2-hydroxyacetophenone, 5-dimethylamino-2-hydroxyacetophenone, 4-N-piperidinyl-2-hydroxyacetophenone, 3-phenoxy-2-hydroxyacetophenone, 4-p-chlorophenoxy-2-hydroxyacetophenone, 5-p-tolyl-2-hydroxyacetophenone, 1-hydroxy-2-acetylnaphthalene and 2-hydroxy-1-acetylnaphthalene.

In addition, the gloxylic acid derivatives of the formula (III) are required as starting compounds. In the formula (III), Z preferably represents an alkali metal cation, an equivalent of an alkaline earth metal cation, an ammonium cation or a monoalkylammonium, dialkylammonium or trialkylammonium cation.

The synthesis is carried out in the presence of a basic compound. As such, it is preferred to use secondary amines, such as open-chain amines, such as dimethylamine and diethylamine, and, more especially, cyclic amines such as pyrrolidine and also piperidine, N-methyl-piperazine and morpholine. The said compounds are generally known.

The process according to the invention can be carried out with or without a solvent. All solvents which are inert towards the starting components and the end product can be used to carry out the process. As examples of solvents there may be mentioned: aliphatic or aromatic hydrocarbons, such as petroleum ether, benzene, toluene or xylene; aliphatic or aromatic halohydrocarbons, such as carbon tetrachloride, chlorobenzene or dichlorobenzene; ethers, such as diethyl ether, tetrahydrofuran, dioxan or glycol dimethyl ether; amides, such as dimethylformamide, dimethylacetamide and N-methylpyrrolidone; esters, such as ethyl acetate; nitriles, such as acetonitrile and propionitrile; alcohols, such as methanol, ethanol and glycol monomethyl ether; water; and mixtures of these solvents.

The process according to the invention can be carried out at a temperature of about −30° C. to +150° C., preferably of about 20° to 80° C.

To carry out the process according to the invention, the o-hydroxycarbonyl compound (II) and the salt of the glyoxylic acid (III) are in general employed in stoichiometric amounts, that is to say in the ratio of about 1:2. However, for the purpose of carrying out the process according to the invention it does not matter if a small excess of one component, especially of the glyoxylic acid salt, is employed (for example up to a molar ratio of about 1:2.5). The amount of the amine employed is not critical. In general, about 0.05 to 1.5, preferably about 0.1 to 1, mole of the amine is used per mole of the o-hydroxycarbonyl compound. If the o-hydroxyacetophenones are substituted by groups with an acid reaction, such as, for example, carboxyl groups, it can be advantageous to neutralize the acid groups by an excess of the amine.

In general, the process according to the invention is carried out as follows:

At the selected reaction temperature, the starting compounds are dissolved, if appropriate in a solvent, and the amine is added. As a result of the exothermic reaction, the reaction temperature in general rises so that further warming is not necessary. The reaction mixture is then left to stand, without further warming, until completion of the reaction, but the reaction time can also be shortened by external warming. After completion of the reaction, the chromone derivative is isolated by dissolving the resulting salt in water and acidifying this solution, for example with a mineral acid such as hydrochloric acid, sulphuric acid or phosphoric acid. The dicarboxylic acid compound of the formula (I), wherein $R^3$ represents hydrogen, is thus obtained.

The esterification of the dicarboxylic acid obtained can be carried out, for example, in the usual manner by stirring the dicarboxylic acid with about a 4-fold to 100-fold, preferably about 10-fold to 50-fold, molar amount of alcohol of the formula $R^3$-OH, adding an acid such as concentrated sulphuric acid or saturating the mixture with hydrogen chloride gas, and warming the whole for a few hours at temperatures of about 60° to 120° C. It is also possible to add an at least twice the molar amount, relative to the dicarboxylic acid, of a dehydrating agent, such as an inorganic acid halide, for example thionyl chloride or phosphorus oxychloride, to the mixture of the dicarboxylic acid with the alcohol. Finally, it is also possible to react a salt of the dicarboxylic acid with at least twice the molar amount of an alkyl halide, in a solvent such as dimethylsulphoxide or dimethylformamide.

As examples of new chromonedicarboxylic acids and their esters there may be mentioned: 2-carboxy-3-carboxymethylchromone, 2-carboxy-3-carboxymethyl-6-chloro-chromone, 2-carboxy-3-carboxymethyl-7-chloro-chromone, 2-carboxy-3-carboxymethyl-8-chloro-chromone, 2-carboxy-3-carboxymethyl-6,8-dichloro-chromone, 2-carboxy-3-carboxymethyl-6-methylchromone, 2-carboxy-3-carboxymethyl-7-methyl-chromone, 2-carboxy-3-carboxymethyl-6-isobutyl-chromone, 2-carboxy-3-carboxymethyl-7-ethyl-chromone, 2-carboxy-3-carboxymethyl-6-sec.-butyl-chromone, 2-carboxy-3-carboxymethyl-6-benzyl-chromone, 2-carboxy-3-carboxymethyl-7-phenyl-chromone, 2-carboxy-3-carboxymethyl-5-methoxy-chromone, 2-carboxy-3-carboxymethyl-6-methoxy-chromone, 2-carboxy-3-carboxymethyl-7-methoxy-chromone, 2-carboxy-3-carboxymethyl-8-methoxy-chromone, 2-carboxy-3-carboxymethyl-6-chloro-8-methylchromone, 2-carboxy-3-carboxymethyl-6-pyrrolidinyl-chromone, 2-carboxy-3-carboxymethyl-6-dimethylamino-chromone, 2-carboxy-3-carboxymethyl-7,8-dimethoxy-chromone, 2-carboxy-3-carboxymethyl-6,7-dimethoxy-chromone, 2-carboxy-3-carboxymethyl-6-methoxycarbonyl-chromone, 2-carboxy-3-carboxymethyl-8-carboxy-chromone, 2-carboxy-3-carboxymethyl-7-cyano-chromone, 2-carboxy-3-carboxymethyl-6-cyanochromone, 2-carboxy-3-carboxymethyl-5,6,7-trimethylchromone, 2-carboxy-3-carboxymethyl-5,6-benzo-chromone, 2-carboxy-3-carboxymethyl-5,6-trimethylene-chromone, 2-carboxy-3-carboxymethyl-5-methyl-6,8-dichloro-chromone, 2-carbomethoxy-3-carbomethoxymethyl-chromone, 2-carbomethoxy-3-carbomethoxymethyl-6-chloro-chromone, 2-carbomethoxy-3-carbomethoxymethyl-7-chloro-chromone, 2-carbomethoxy-3-carbomethoxymethyl-6,8-dichloro-chromone, 2-carbomethoxy-3-carbomethoxymethyl-6-methyl-chromone, 2-carbomethoxy-3-carbomethoxymethyl-7-methyl-chromone, 2-carbomethoxy-3-carbomethoxymethyl-6-isobutyl-chromone, 2-carbomethoxy-3-carbomethoxymethyl-6-cyclopentyl-chromone, 2-carbomethoxy-3-carbomethoxymethyl-7-phenyl-chromone, 2-carbomethoxy-3-carbomethoxymethyl-5-methoxy-chromone, 2-carbomethoxy-3-carbomethoxymethyl-6-methoxy-chromone, 2-carbomethoxy-3-carbomethoxymethyl-7-methoxy-chromone, 2-carbomethoxy-3-carbomethoxymethyl-8-methoxy-chromone, 2-carbomethoxy-3-carbomethoxymethyl-6-chloro-8-methylchromone, 2-carbomethoxy-3-carbomethoxymethyl-7,8-dimethoxychromone, 2-carbomethoxy-3-carbomethoxymethyl-6,7-dimethoxychromone, 2-carbomethoxy-3-carbomethoxymethyl-8-carboxychromone, 2-carbomethoxy-3-carbomethoxymethyl-6-cyanochromone, 2-carbomethoxy-3-carbomethoxymethyl-5,6-benzochromone, 2-carbomethoxy-3-carbomethoxymethyl-5-methyl-6,8-dichloro-chromone, 2-carboethoxy-3-carbo-ethoxymethylchromone, 2-carbopropoxy-3-carbopropoxymethylchromone, 2-carbo-isopropoxy-3-carbo-isopropoxymethylchromone, 2-carbobutoxy-3-carbobutoxymethylchromone, 2-carbo-sec.-butoxy-3-carbo-sec.-butoxymethylchromone, 2-carbo-isobutoxy-3-carbo-iso-butoxymethylchromone, 2-carbo-tert.-butoxy-3-carbo-tert.-butoxymethylchromone, 2-carbobenzyloxy-3-carbobenzyloxymethylchromone, 2-carbophenethoxy-3-carbophenethoxymethylchromone, 2-carbocyclopentyloxy-3-carbocyclopentyloxymethylchromone, 2-carbocyclohexyloxy-3-carbocyclohexyloxymethylchromone, 2-carboallyloxy-3-carboallyloxymethylchromone, 2-carbo-p-chlorobenzyloxy-3-carbo-p-chlorobenzyloxymethylchromone, 2-carbo-(2'-methoxy)ethoxy-3-carbo-(2'-methoxy)-ethoxymethylchromone and 2-carbo(2'-bromo)-ethoxy-3-carbo-2'-(bromo)-ethoxymethylchromone.

The active compounds according to the invention exhibit a powerful fungitoxic action. They do not damage crop plants in the concentrations required for combating fungi. For these reasons, they are suitable for use as plant protection agents for combating fungi. Fungitoxic agents are employed in plant protection for combating Plasmodiophoromycetes, Oomycetes, Chytridiomycetes, Zygomycetes, Ascomycetes, Basidiomycetes and Deuteromycetes.

The active compounds according to the invention can be used against parasitic fungi and bacteria which attack above-ground parts of plants or attack the plants through the soil, as well as against seed-borne pathogens.

The good toleration by plants permits the active compounds to be used against fungal plant diseases by treating the standing crop plant or individual parts thereof or by treating the seed or even by treating the culture soil. The active compounds are particularly active against cereal mildew.

The active compounds can be converted into the customary formulations, such as solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid solvents diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone of cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

The formulations in general contain from 0.1 to 95 percent by weight of active compound, preferably from 0.5 to 90 percent.

The active compounds can be used as such, as their formulations or as the use forms prepared therefrom by further dilution, such as ready-to-use solutions, emulsions, suspensions, powders, pastes and granules. They may be used in the customary manner, for example by watering, spraying, atomizing, dusting, scattering, dry dressing, moist dressing, wet dressing, slurry dressing or encrusting.

The active compound content of the use forms prepared from the formulations of the types that are commercially available can vary within wide ranges. The active compound concentration of the use forms can be from 0.0000001 to 100% by weight of active compound, preferably from 0.01 to 10% by weight.

For dressing, amounts of active compound of 10 mg to 10 g, preferably 100 mg to 3 g, are in general used per kilogram of seed. For the treatment of soil, which can be carried out over the whole area, in strips or at points, active compound concentrations of 1 to 1,000 g of active compound per m³ of soil, preferably 10 to 200 g per m³, are generally employed at the locus of the expected action.

As already mentioned, the compounds according to the invention inhibit the development of arthropods.

The present invention also provides fungicidal or arthropodicidal compositions containing as active ingredient a compound of the present invention in admixture with a solid or liquefied gaseous diluent or carrier or in admixture with a liquid diluent or carrier containing a surface-active agent.

The present invention also provides a method of combating fungi or arthropods which comprises applying to the fungi or arthropods, or to a habitat thereof, a compound of the present invention alone or in the form of a composition containing as active ingredient a compound of the present invention in admixture with a diluent or carrier.

The present invention further provides crops protected from damage by fungi or arthropods by being grown in areas in which immediately prior to and/or during the time of the growing a compound of the present invention was applied alone or in admixture with a diluent or carrier.

It will be seen that the usual methods of providing a harvested crop may be improved by the present invention.

The preparation of the novel compounds is shown in the following illustrative examples:

EXAMPLE 1

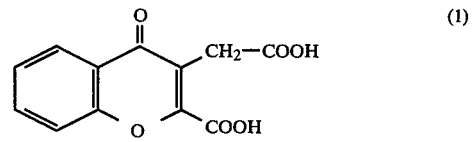

(1)

75 g (0.55 mol) of o-hydroxyacetophenone and 350 ml of water/ice were stirred with 60 ml of pyrrolidine. 250 g of sodium glyoxylate (hydrate, about 50% strength; 1.1 mol) were added to the clear solution and the mixture was stirred further, without cooling. After a few hours, the salt had given an almost clear solution; later, a part of the end product separated out as the disodium salt. After 5 days, about 600 ml of water were added, stirring was continued until an almost clear solution resulted, and concentrated hydrochloric acid was added to the filtrate until a pH value of 1 was reached. The precipitate which separated out was filtered off after 1 day, and dried. Yield: 125 g of 2-carboxy-3-carboxymethyl-chromone, of melting point 240°–242° C., representing 92% of theory.

EXAMPLE 1a

The procedure described in Example 1 was followed, but after mixing the starting materials the batch was warmed for 30 minutes to 95° C. Working up gave 112 g of 2-carboxy-3-carboxymethyl-chromone, representing 82% of theory.

EXAMPLE 2

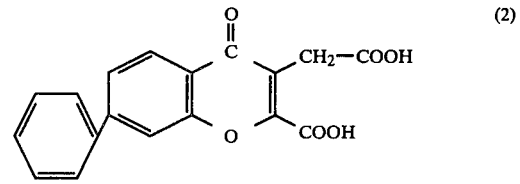

(2)

63 g of 4-phenyl-2-hydroxyacetophenone, 700 ml of isopropanol and 110 g of a 50% strength solution of glyoxylic acid in water were stirred and 63 g of pyrrolidine were added at a temperature below 0° C. After 6 days, the resulting solution was diluted with 1 liter of water and acidified. Yield: 22 g of 2-carboxy-3-carboxymethyl-7-phenyl-chromone of melting point 219°-221° C.

EXAMPLE 3

(Esterification reaction)

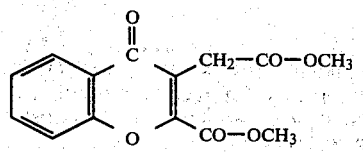

220 g of 2-carboxy-3-carboxymethyl-chromone (prepared according to Example 1) were stirred into 2 liters of methanol, hydrogen chloride gas was introduced until saturation was reached and the mixture was warmed at the same time, until the reflux temperature was reached. After 8 hours, the mixture as allowed to cool and the product was filtered off. 196 g of 2-carbomethoxy-3-carbomethoxymethyl-chromone of melting point 105° C. were obtained.

EXAMPLE 3a (Esterification reaction; compare Example 3)

15 g of 2-carboxy-3-carboxymethyl-chromone were stirred into 60 ml of methanol, and 15 ml of thionyl chloride were added in the course of about 10 minutes, while keeping the temperature below 35° C. The mixture was then heated to 60° C. over the course of 2 hours, and was allowed to cool, and the product was filtered off. 13.5 g of the same product as described in Example 3 were obtained.

EXAMPLE 4

(Esterification reaction)

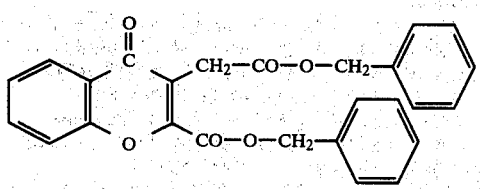

25 g of 2-carboxy-3-carboxymethyl-chromone were dissolved in 30 ml of dimethylsulphoxide, and 30 ml of triethylamine and 30 g of benzyl chloride were added successively. After 24 hours the mixture was poured onto ice water and was extracted by shaking with chloroform, and the chloroform layer was washed with 100 ml of 2-normal sodium hydroxide solution and then with water. After drying and concentrating, a residue was obtained, which was recrystallized from ether. The yield was 17 g of 2-benzyloxycarbonyl-3-benzyloxycarbonylmethyl-chromone of melting point 82°-84° C.

The following compounds of the general formula

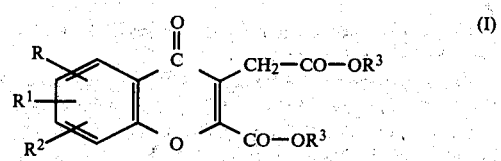

could be prepared in a similar manner to that described in Examples 1 to 4.

TABLE 1

| Compound No. | R | $R^1$ | $R^2$ | $R^3$ | Yield % of theory | Melting point (°C.) |
|---|---|---|---|---|---|---|
| 5 | 6-Cl | H | H | H | 77 | 219-221 |
| 6 | 7-Cl | H | H | H | 84 | 150-152 |
| 7 | 6-Cl | 8-Cl | H | H | 66 | 230-232 |
| 8 | 6-Cl | 8-$CH_3$ | H | H | 74 | 170-172 |
| 9 | 6-$CH_3O$ | H | H | H | 77 | 225-227 |
| 10 | 7-$CH_3O$ | H | H | H | 61 | 239-241 |
| 11 | 7-$CH_3O$ | 8-$CH_3O$ | H | H | 80 | 230-232 |
| 12 | 6-$CH_3$ | H | H | H | 83 | 204-206 |
| 13 | 7-$CH_3$ | H | H | H | 64 | 147-148 |
| 14 | 5,6-CH=CH—CH=CH | | H | H | 51 | decomposes above 150 |
| 15 | H | H | H | $C_2H_5$ | 60 | 63-65 |
| 16 | 7-$CH_3O$ | H | H | $CH_3$ | 87 | 118-120 |
| 17 | 6-Cl | 8-Cl | H | $CH_3$ | 90 | 139-141 |
| 18 | 6-Cl | H | H | $CH_3$ | 88 | 169-171 |
| 19 | 7-Cl | H | H | $CH_3$ | 87 | 147-148 |
| 20 | 7-$CH_3$ | H | H | $CH_3$ | 70 | 123-125 |
| 21 | 6-Cl | 8-$CH_3$ | H | $CH_3$ | 65 | 138-141 |
| 22 | 7-$CH_3O$ | 8-$CH_3O$ | H | $CH_3$ | 63 | 163-165 |
| 23 | 6-$CH_3$ | H | H | $CH_3$ | 51 | 155-157 |

The example given below illustrates the arthropod metamorphosis-inhibiting action of the compounds according to the invention, without intending a limitation in respect of the breadth of action of these compounds. In the experiments, the morphological changes, such as half-pupated insects, incompletely slipped larvae or caterpillars, defective wings and pupal cuticula of imagines, as well as the mortality, were assessed over the entire stated development of the test insects. The sum of the morphological malformations and of the destruction during development was assessed.

EXAMPLE 5

Development-inhibiting action/ingestion test

Test insects:
Plutella maculipennis (caterpillars in the 4th state of development, 20 specimens)
Phaedon cochleariae (larvae in the 4th stage of development, 20 specimens)
Feed plants: Cabbage plants (Brassica oleracea)
Solvent: 4 parts by weight of acetone
Emulsifier: 1 part by weight of alkylaryl polyglycol ether To produce a suitable preparation of active compound, 2 parts by weight of active compound were mixed with the stated amounts of solvent and of emulsifier and with sufficient water to give a 1% strength mixture, which was diluted with water to the desired concentration.

The test animals were fed with leaves of the feed plants, which were provided with a uniform spray covering of the active compound mixture of the desired concentrations, so that the prescribed amounts of active compound in ppm (parts per million) were obtained on the leaves, until the imago developed.

As a control, leaves provided only with solvent and emulsifier of the prescribed concentration were used as the feed.

Evaluation of the experiments showed that, in particular, compounds 3, 5 and 10 according to the invention were superior to a known comparison formulation to a known comparison formulation (2,2-dimethyl-6-methoxy-benzopyran).

The fungicidal activity of the compounds of this invention is illustrated by the following example wherein the compounds according to the present invention are each identified by the number (given in brackets) from the preparative examples hereinabove.

The known comparison compound is identified as follows:

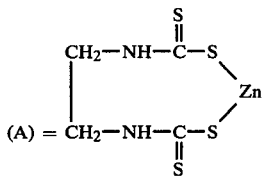

EXAMPLE 6

Shoot treatment test/powdery mildew of cereals (leaf-destructive mycosis)/protective To produce a suitable preparation of active compound, 0.25 part by weight of active compound was taken up in 25 parts by weight of dimethylformamide and 0.06 part by weight of alkylaryl polyglycol ether; 975 parts by weight of water were then added. The concentrate was diluted with water to the desired final concentration of the spray liquor.

To test for protective activity, single-leaved young barley plants of the Amsel variety were sprayed with the preparation of active compound until dew-moist. After drying, the barley plants were dusted with spores of *Erysiphe graminis* var. *hordei*.

After 6 days' dwell time of the plants at a temperature of 21–22 deg.C. and 80–90% atmospheric humidity the occurrence of mildew pustules on the plants was evaluated. The degree of infection was expressed as a percentage of the infection of the untreated control plants. 0% denoted no infection and 100% denoted the same degree of infection as in the case of the untreated control. The more active the compound, the lower was the degree of mildew infection.

The active compounds, active compound concentrations in the spray liquor and degrees of infection can be seen from the table which follows:

TABLE 2

Shoot treatment test/powdery mildew of cereals/protective

| Active compounds | Active compound concentration in the spray liquor in % by weight | Infection in % of the untreated control |
|---|---|---|
| untreated | — | 100.0 |
| (A) | 0.025 | 100.0 |
| (3) | 0.025 | 0.0 |
| (16) | 0.025 | 20.0 |
| (18) | 0.025 | 38.5 |

It will be appreciated that the instant specification and examples are set forth by way of illustration and not limitation, and that various modifications and changes may be made without departing from the spirit and scope of the present invention.

What we claim is:

1. A process for the preparation of a compound of the formula

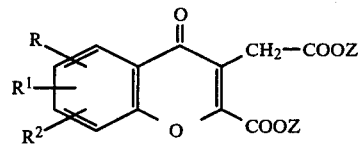

in which

R, $R^1$ and $R^2$ each independently is hydrogen, an alkyl, alkenyl, cycloalkyl, cycloalkenyl, aralkyl or an aryl group, halogen, hydroxyl, cyano or an alkoxy, aryloxy, aralkoxy, alkoxycarbonyl or dialkylamino group, or R and $R^1$ together with two carbon atoms of the benzene ring system, form a carbocyclic 5-membered or 6-membered, furan, thiophene, dihydrothiophene, pyrane, dihydropyrane, pyridine or dioxolene ring, and Z is a cation, comprising reacting an o-hydroxyacetophenone of the formula

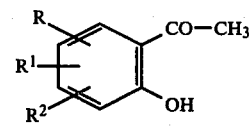

with a glyoxylic acid derivative of the formula

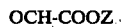

in which Z is a cation, in the presence of a secondary amine.

2. A process according to claim 1, in which the secondary amine is pyrrolidine, piperidine, N-methyl-piperazine, morpholine, dimethylamine or diethylamine.

3. A pocess according to claim 1 in which the reaction is carried out at from about −30° to +150° C.

4. A process according to claim 1, in which the reaction is effected in the presence of an inert organic solvent or water.

5. A process according to claim 1, in which Z is an alkali metal cation, an equivalent of an alkaline earth metal, an ammonium cation or a monoalkylammonium, dialkylammonium or trialkylammonium cation.

6. A process according to claim 1, in which about 2 to 2.5 moles of the glyoxylic acid derivative are employed per mole of the o-hydroxyacetophenone.

7. A process according to claim 1, in which about 0.05 to 1.5 moles of the secondary amine are used per mole of the o-hydroxyacetophenone.

8. A process according to claim 1, including the further steps of acidifying the reaction mass thereby to form the dicarboxylic acid wherein both Z's are converted to hydrogen.

9. A process according to claim 8, including the further step of reacting the dicarboxylic acid with about 4 to 100 times its molar amount of an alcohol of the formula

wherein $R^3$ is alkyl, alkenyl, cycloalkyl, cycloalkenyl or aralkyl, in the presence of an acid to replace both Z's by $R^3$.

10. A process according to claim 9, wherein R, $R^1$ and $R^2$ are hydrogen and $R^3$ is $CH_3$.

11. A process according to claim 9, wherein R and $R^1$ are hydrogen, $R^2$ is 7-$OCH_3$, and $R^3$ is $CH_3$.

12. A process according to claim 9, wherein R and $R^1$ are hydrogen, $R^2$ is 6-Cl, and $R^3$ is $CH_3$.

* * * * *